United States Patent
Tezuka

(10) Patent No.: US 9,757,086 B2
(45) Date of Patent: Sep. 12, 2017

(54) RADIATION IMAGING SYSTEM, CONTROL METHOD THEREFOR, AND STORAGE MEDIUM HAVING STORED THEREON A PROGRAM FOR EXECUTING THE CONTROL METHOD

(71) Applicant: CANON KABUSHIKI KAISHA, Tokyo (JP)

(72) Inventor: Shimpei Tezuka, Shimotsuke (JP)

(73) Assignee: CANON KABUSHIKI KAISHA, Tokyo (JP)

(*) Notice: Subject to any disclaimer, the term of this patent is extended or adjusted under 35 U.S.C. 154(b) by 34 days.

(21) Appl. No.: 14/959,175

(22) Filed: Dec. 4, 2015

(65) Prior Publication Data

US 2016/0157810 A1    Jun. 9, 2016

(30) Foreign Application Priority Data

Dec. 9, 2014 (JP) ................................. 2014-249261

(51) Int. Cl.
*A61B 6/04* (2006.01)
*A61B 6/00* (2006.01)

(52) U.S. Cl.
CPC .............. *A61B 6/54* (2013.01); *A61B 6/4405* (2013.01); *A61B 6/5294* (2013.01); *A61B 6/56* (2013.01); *A61B 6/586* (2013.01)

(58) Field of Classification Search
CPC ....... A61B 6/4429; A61B 6/467; A61B 6/463; A61B 6/0407; A61B 6/5229;
(Continued)

(56) References Cited

U.S. PATENT DOCUMENTS

2007/0267565 A1* 11/2007 Nishizawa ............ H01J 43/246
                                                                    250/207
2009/0141022 A1    6/2009 Kimpe et al.
2012/0323100 A1   12/2012 Kamath et al.

FOREIGN PATENT DOCUMENTS

JP    2002-190584 A    7/2002
JP    2002-248095 A    9/2002
(Continued)

OTHER PUBLICATIONS

Russian Office Action dated May 25, 2017 in corresponding Russian Patent Application No. 2015152464 together with English translation, 9 pages.

(Continued)

*Primary Examiner* — Don Wong
(74) *Attorney, Agent, or Firm* — Carter, DeLuca, Farrell & Schmidt, LLP

(57) ABSTRACT

A radiation imaging system including: a radiation imaging apparatus for obtaining a captured image by radiographic image capturing of a subject; and an external apparatus connectable to the radiation imaging apparatus, the external apparatus including a system time management unit for managing a system time serving as a reference time of the radiation imaging system, the radiation imaging apparatus including: an imaging apparatus time management unit for managing an imaging apparatus time, which is a time on the radiation imaging apparatus; a storing unit for storing image capturing information in association with the captured image obtained by the radiographic image capturing, the image capturing information including at least image capturing time information which is determined based on the imaging apparatus time; and a time correction unit for obtaining the (Continued)

system time and correcting the image capturing time information based on the imaging apparatus time and the system time.

19 Claims, 5 Drawing Sheets

(58) Field of Classification Search
CPC ... A61B 6/4233; A61B 6/4405; A61B 6/4283;
G06T 2207/10081; G06T 2207/10116;
G06F 19/322
USPC ....... 378/91, 162, 176, 98.8, 62; 250/370.09
See application file for complete search history.

(56) References Cited

FOREIGN PATENT DOCUMENTS

| | | |
|---|---|---|
| JP | 2009-219585 A | 10/2009 |
| JP | 2011-249891 A | 12/2011 |
| JP | 2012-035009 A | 2/2012 |
| RU | 2256169 C1 | 7/2005 |

OTHER PUBLICATIONS

Russian Search Report completed on May 24, 2017 in corresponding Russian Patent Application No. 2015152464 together with English translation, 4 pages.

\* cited by examiner

RADIATION IMAGING SYSTEM, CONTROL METHOD THEREFOR, AND STORAGE MEDIUM HAVING STORED THEREON A PROGRAM FOR EXECUTING THE CONTROL METHOD

BACKGROUND OF THE INVENTION

Field of the Invention

The present invention relates to a radiation imaging system including a radiation imaging apparatus configured to obtain a captured image by radiographic image capturing of a subject, and an external apparatus configured to be connectable to the radiation imaging apparatus, and also relates to a control method therefor and a storage medium having stored thereon a program for executing the control method.

Description of the Related Art

There have hitherto been known radiation imaging apparatus products and radiation imaging system products in which a radiation generation apparatus irradiates a subject with a radiation ray, the intensity distribution of a portion of the radiation ray that is transmitted through the subject is converted into digital signals to generate a radiographic image that is a captured image, and image processing is performed on the radiographic image to obtain a sharp radiographic image.

In such radiation imaging systems, a radiation generation apparatus emits a radiation ray and a radiation imaging apparatus transfers image data of a generated radiographic image to an image processing apparatus such as a control computer for image processing and saving.

A radiation imaging apparatus generally includes a sensor array in which pixels are arranged two-dimensionally and each pixel includes a conversion element configured to convert radiation into signal charges (electric signals) and a switching element, such as a TFT, configured to transfer the electric signals to the outside. The radiation imaging apparatus executes matrix driving with the use of the switching element such as a TFT, to thereby read signal charges generated by the conversion in the conversion element and form a radiographic image from digital signals based on the charge amount of the read signal charges.

In recent years, technologies with which a radiation imaging apparatus itself detects the start/end of radiation irradiation have been proposed, and an example of the technologies can be found in Japanese Patent Application Laid-Open No. 2011-249891. Those technologies eliminate the need for a mechanism that synchronizes the radiation imaging apparatus and the radiation generation apparatus. As a result, the construction of the radiation imaging apparatus is simplified and cable connection between the radiation imaging apparatus and the radiation generation apparatus is rendered unnecessary. A rechargeable battery included inside the radiation imaging apparatus also makes it unnecessary to connect a power supply cable for the feeding of power, thereby improving the portability of the radiation imaging apparatus further.

In Japanese Patent Application Laid-Open No. 2002-190584, there has been proposed an apparatus configured to record image information obtained by image capturing with the use of a portable memory that is removably mounted to the main body of a radiation imaging apparatus. In Japanese Patent Application Laid-open No. 2002-248095, there has been proposed an apparatus configured to transfer, when loaded in a cradle capable of charging a battery of an imaging apparatus, a captured image to an external apparatus via the cradle. Apparatus as those do not need to connect a cable for image transfer or build a wireless communication environment, and can accordingly be built even more simply and are improved in the portability of the imaging apparatus itself.

However, it is difficult with those apparatus to identify the situation of the image capturing that has produced the transferred image information. Identifying the image capturing information of a handed over image can be particularly difficult when images of different subjects captured by a plurality of imaging apparatus or under different image capturing conditions are transferred after a long time.

An apparatus designed to solve this problem has been proposed in, for example, Japanese Patent Application Laid-Open No. 2009-219585. Specifically, the proposed apparatus attempts to solve the problem by controlling a cradle that is capable of loading a plurality of imaging apparatus therein so that only one of the imaging apparatus that is selected by an image capturing order can be used, while the unselected imaging apparatus are locked to prevent removal from the cradle.

In Japanese Patent Application Laid-Open No. 2012-35009, there has been proposed a technology in which a memory is provided in a battery apparatus configured so as to be removably mounted to an imaging apparatus, image capturing information of scheduled image capturing is stored in the memory in advance at the time the battery is charged, and image data is saved in association with the image capturing information when the image is captured. This technology can prevent wrong association between a captured image obtained by image capturing and image capturing information that includes patient information and image capturing conditions.

In Japanese Patent Application Laid-Open No. 2009-219585 and Japanese Patent Application Laid-Open No. 2012-35009, wrong association between image capturing information that includes, for example, patient information, and a captured image itself is avoided by determining which radiation imaging apparatus is to be used based on an image capturing order received in advance. However, it can easily happen in an emergency case or the like that image capturing is demanded without the advance submission of an image capturing order or the advance entering of patient information. In such cases, image capturing information needs to be associated with image data at a separate time after the image data is obtained.

A possible way to accomplish this includes recording, together with the captured image data, image capturing execution information that can be recorded without the advance input, such as the ID of the imaging apparatus that has been used for the image capturing, a captured image ID, and time information about the date/time of execution of the image capturing, and, when the captured image data is transferred subsequently, manually adding image capturing information such as patient information based on those pieces of image capturing execution information.

Of the pieces of information that can be recorded without the advance input, the time information about the date/time of execution of the image capturing is particularly useful in associating the image capturing information later. However, there is a fear in that the time kept by an internal clock of a radiation imaging apparatus does not match a system time on an external apparatus to which the image is transferred, and there may accordingly be a disparity between the system time and the time information about the date/time of image capturing. In the case where image capturing is executed with the use of a plurality of imaging apparatus, in particular, times that are indicated by recorded pieces of image capturing time information may not match the actual order of image capturing because the amount of the disparity of the internal clock varies from one imaging apparatus to another. This can invite confusion when image capturing information that includes patient information (subject information) is manually associated later.

Providing each imaging apparatus with a highly precise clock such as an atomic clock could be a solution, but this complicates the structure of the imaging apparatus. In addition, constantly securing a radio wave environment to correct time is difficult for radiation imaging apparatus, which are used mostly in a room structured so as to cut off radiation because of their nature.

SUMMARY OF THE INVENTION

One aspect of the present invention has been made in view of those problems, and the present invention provides a mechanism capable of reducing, with a simple configuration, the risk of wrong association between a captured image and a piece of image capturing information in the case where image capturing information that includes subject information is associated with a captured image at a later point.

According to one embodiment of the present invention, there is provided a radiation imaging system, including: a radiation imaging apparatus configured to obtain a captured image by radiographic image capturing of a subject; and an external apparatus configured to be connectable to the radiation imaging apparatus, the external apparatus including a system time management unit configured to manage a system time, which serves as a reference time of the radiation imaging system, the radiation imaging apparatus including: an imaging apparatus time management unit configured to manage an imaging apparatus time, which is a time on the radiation imaging apparatus; a storing unit configured to store image capturing information in association with the captured image obtained by the radiographic image capturing, the image capturing information including at least image capturing time information about a date/time of execution of the radiographic image capturing which is determined based on the imaging apparatus time; and a time correction unit configured to obtain the system time and to correct the image capturing time information based on an amount of a time disparity between the imaging apparatus time and the system time.

According to another embodiment of the present invention, there is provided a radiation imaging system, including: a radiation imaging apparatus configured to obtain a captured image by radiographic image capturing of a subject; a portable power supply apparatus including a rechargeable power supply unit configured to run the radiation imaging apparatus, the portable power supply apparatus being removably mounted to the radiation imaging apparatus; and an external apparatus configured to be connectable to the portable power supply apparatus, the portable power supply apparatus including: an imaging apparatus time management unit configured to manage an imaging apparatus time, which is a time on the radiation imaging apparatus; and a storing unit configured to store image capturing information in association with the captured image obtained by the radiographic image capturing, the image capturing information including at least image capturing time information about a date/time of execution of the radiographic image capturing which is determined based on the imaging apparatus time, the external apparatus including: a system time management unit configured to manage a system time, which serves as a reference time of the radiation imaging system; and a time correction unit configured to obtain the imaging apparatus time and to correct the image capturing time information based on an amount of a time disparity between the imaging apparatus time and the system time.

Further, according to another embodiment of the present invention, there are provided a method of controlling the radiation imaging system and a storage medium having stored thereon a program for executing the control method.

Further features of the present invention will become apparent from the following description of exemplary embodiments with reference to the attached drawings.

DESCRIPTION OF THE EMBODIMENTS

Modes for carrying out the present invention (embodiments) are described below with reference to the drawings.

First Embodiment

A first embodiment of the present invention is described first.

Figure 1:
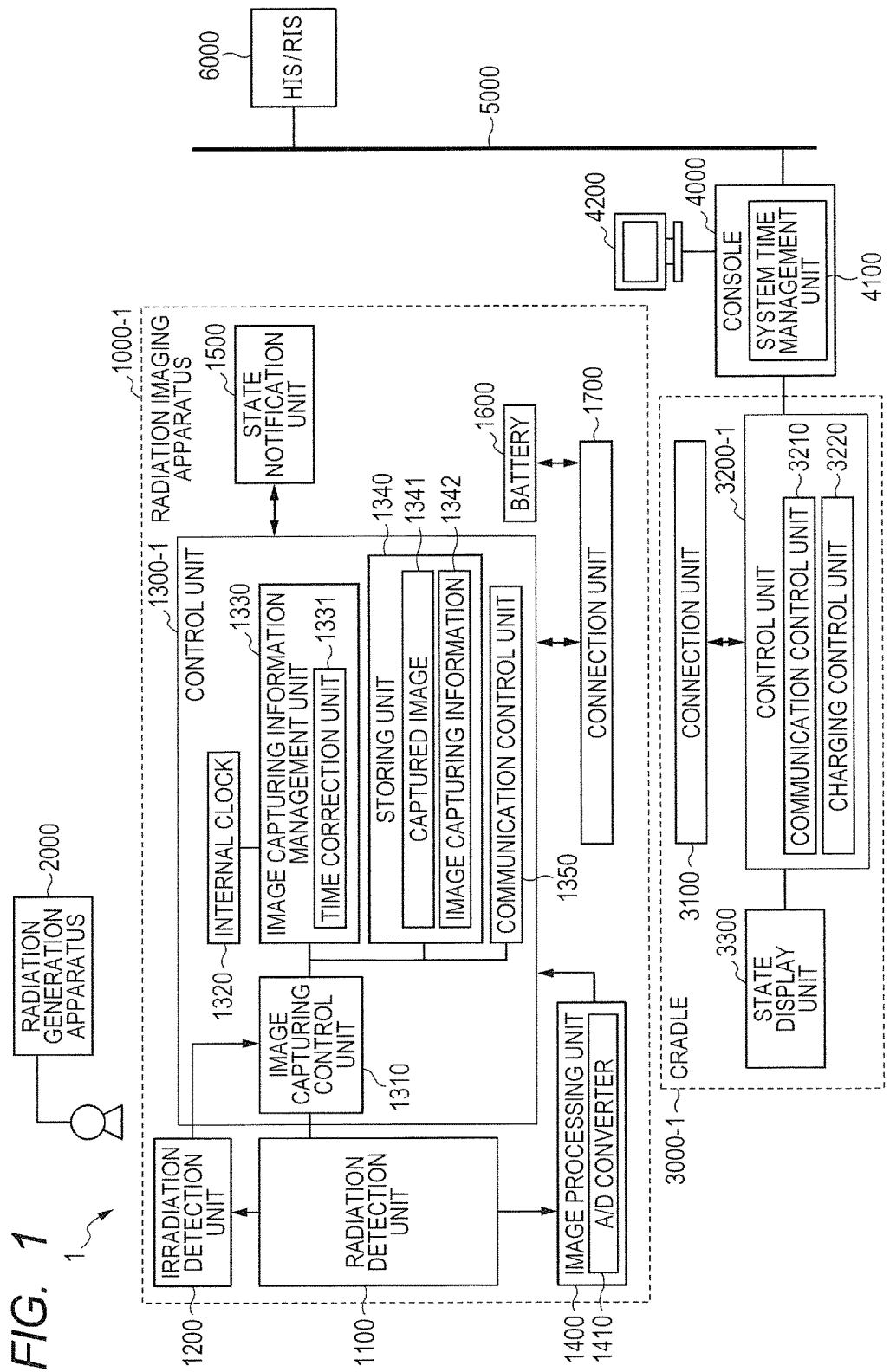
FIG. 1 is a diagram for illustrating an example of the schematic configuration of a radiation imaging system according to a first embodiment of the present

FIG. 1 is a diagram, for illustrating an example of the schematic configuration of a radiation imaging system 1 according to the first embodiment of the present invention. The radiation imaging system 1 according to this embodiment includes, as illustrated in FIG. 1, a radiation imaging apparatus 1000-1, a radiation generation apparatus 2000, a cradle 3000-1, a console 4000, an intra-hospital network 5000, and an HIS/RIS 6000. Specifically, the radiation imaging system 1 of this embodiment is a system that includes the radiation imaging apparatus 1000-1 configured to obtain a captured image by radiographic image capturing of a subject, and external apparatus (the cradle 3000-1, the console 4000, and the HIS/RIS 6000), which can be electrically connected to the radiation imaging apparatus 1000-1.

The radiation imaging apparatus 1000-1 is an apparatus configured to obtain a radiographic image that is a captured image by radiography based on a portion of a radiation ray that is transmitted through a subject (not shown). The radiation generation apparatus 2000 is an apparatus configured to irradiate the subject (not shown) with a radiation ray. The cradle 3000-1 is an apparatus configured to be capable of charging a battery 1600 within the radiation imaging apparatus 1000-1. The console 4000 is an apparatus capable of collecting and displaying captured images, receiving an image capturing order, and registering image capturing information. The console 4000 is connected to the intra-hospital network 5000, which is built from, for example, a local area network (LAN). The HIS/RIS 6000, which is a hospital information system (HIS) or a radiology information system (RIS), is also connected to the infra-hospital network 5000. The console 4000 and the HIS/RIS 6000 can hold communication to and from each other to exchange an image capturing order for capturing a radiographic image, image capturing information that includes, for example, patient information (subject information), and captured image data itself.

The radiation imaging apparatus 1000-1 includes, as illustrated in FIG. 1, a radiation detection unit 1100, an irradiation detection unit 1200, a control unit 1300-1, an image processing unit 1400, a state notification unit 1500, the battery 1600, and a connection unit 1700.

The radiation detection unit 1100 detects radiation and generates image data of a radiographic image that is a captured image. The radiation detection unit 1100 has pixels each of which includes a TFT or a similar switching element and a photoelectric conversion element and which are arranged two-dimensionally (for example, in a two-dimensional array pattern). For example, a scintillator that converts radiation into visible light is provided above each photoelectric conversion element in this case. Then, a radiation ray entering the radiation detection unit 1100 is converted into visible light by the scintillator, the visible light created by the conversion enters the photoelectric conversion element of each pixel, and the photoelectric conversion element generates electric charges (electric signals) in an amount, determined by the visible light. In this embodiment, the scintillator and the photoelectric conversion element serve as a "conversion element", which converts an incident radiation ray into electric charges. However, the conversion element may instead be, for example, what is called a direct conversion type, which does not include a scintillator and converts an incident radiation ray directly into electric charges. The radiation detection unit 1100 is defined as a component capable of executing the accumulation of electric charges and the readout of electric charges by switching on/off the switching element to obtain a radiographic image that is a captured image. Details of the radiation detection unit 1100 are described below with reference to FIG. 2 and FIG. 3.

Figure 2:
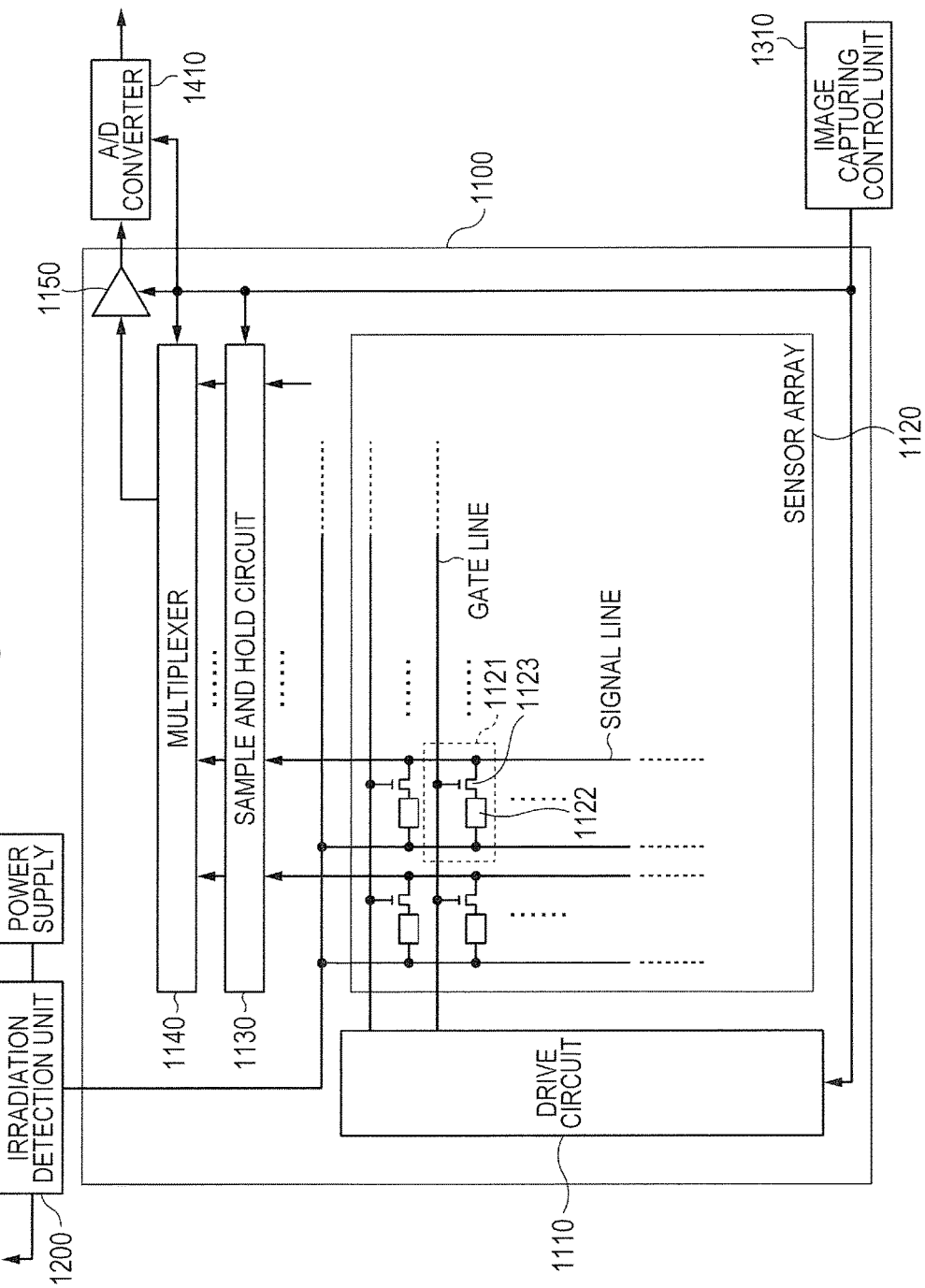
FIG. 2 is a diagram for illustrating an example of the schematic configuration of a radiation detection unit that is illustrated in FIG. 1.

FIG. 2 is a diagram for illustrating an example of the schematic configuration of the radiation detection unit 1100 that is illustrated in FIG. 1. Other than the schematic configuration of the radiation detection unit 1100, the irradiation detection unit 1200, an image capturing control unit 1310, which is a component of the control unit 1300-1, and an A/D converter 1410, which is a component of the image processing unit 1400, are illustrated in FIG. 2.

The radiation detection unit 1100 includes, as illustrated in FIG. 2, a drive circuit 1110, a sensor array 1120, a sample and hold circuit 1130, a multiplexer 1140, and an amplifier 1150. In the sensor array 1120, pixels 1121 each including a conversion element 1122 and a switching element 1123 are arranged two-dimensionally (specifically, in a two-dimensional array pattern). Each conversion element 1122 detects a portion of a radiation ray that is transmitted through a subject, and an array of conversion elements 1122 corresponds to a plurality of radiation detection elements arranged two-dimensionally.

The pixels 1121 in a row of the sensor array 1120 are addressed simultaneously by the drive circuit 1110, and electric charges of each of the pixels 1121 in the row are held in the sample and hold circuit 1130. After being held, the electric charges output from the pixels are read sequentially via the multiplexer 1140, amplified by the amplifier 1150, and then converted into digital signals by the A/D converter 1410. Each time the scanning of one row is finished, the drive circuit 1110 drives and scans the next row of the sensor array 1120 in order, and all electric charges output from pixels are ultimately converted into digital signals. Image data of a radiographic image is read in this manner. In the scanning, reset scanning is accomplished by fixing a voltage that is applied to each column signal line to a particular value and discarding the read electric charges, thus discharging dark electric charges from the pixels. The driving operation and readout operation of the radiation detection unit 1100 are controlled by the image capturing control unit 1310. Image data of a radiographic image that is created by conversion into digital signals is stored in a storing unit 1340 of FIG. 1 as image data of a captured image 1341.

While image data of a radiographic image is stored in the storing unit 1340 here, image data of an offset image which is obtained separately without the irradiation of a radiation ray may be used to store an image obtained by subjecting image data of a radiographic image to offset correction as the captured image 1341 in the storing unit 1340. Other than offset correction, corrective image processing for correcting the characteristics of the radiation detection unit 1100, such as the correction of a defective pixel, may be performed to store a corrected image as the captured image 1341 in the storing unit 1340. The irradiation detection unit 1200, which is configured to detect the start and end of the irradiation of a radiation ray, may include a radiation detection sensor independent of the radiation detection unit 1100 configured to obtain the captured image 1341. However, the radiation detection unit 1100 can detect the start and end of radiation irradiation on its own by, for example, monitoring the amount of dark electric charges that are discharged during the above-mentioned reset scanning of the radiation detection unit 1100.

Figure 3:
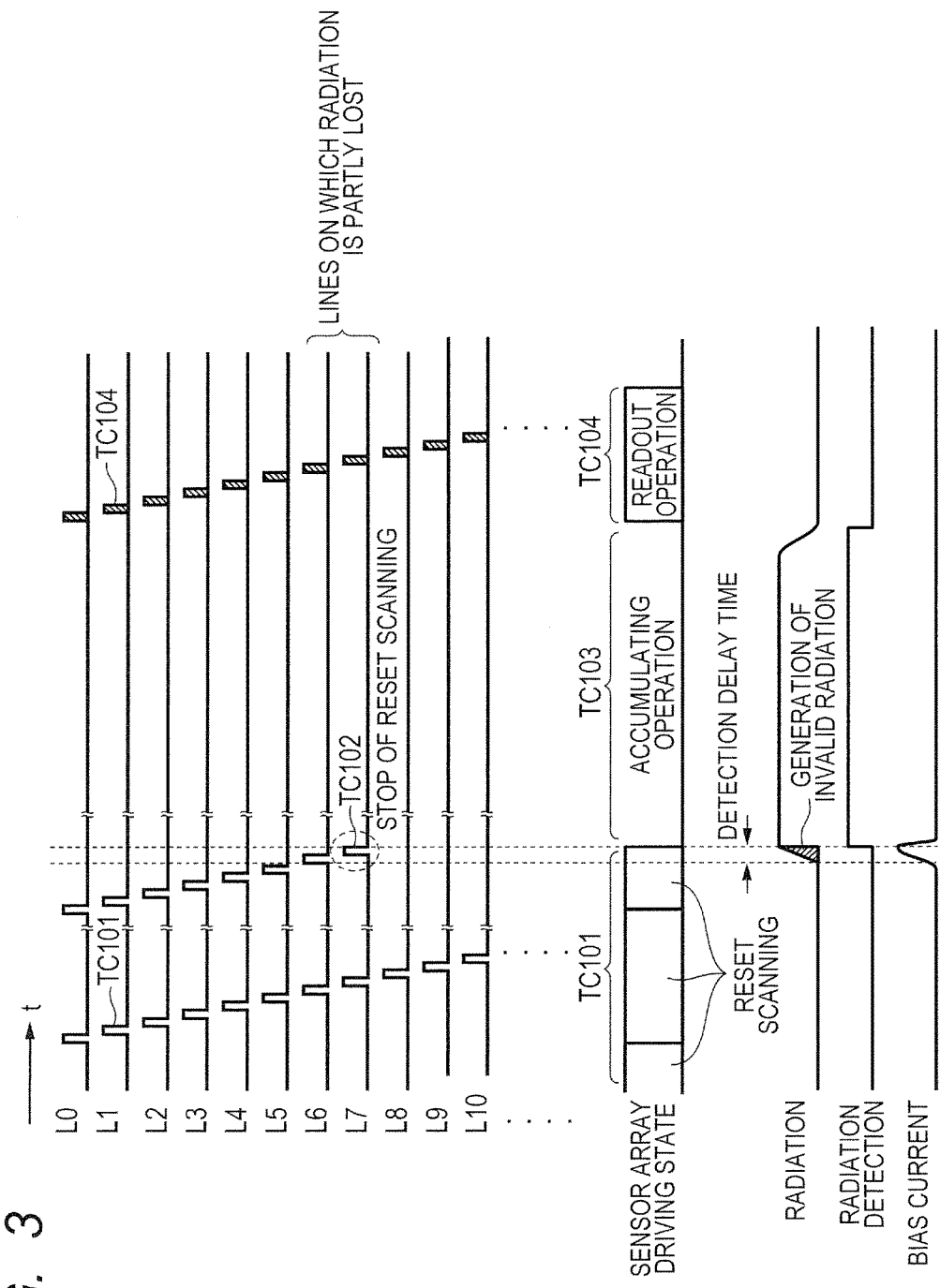
FIG. 3 is a timing chart for illustrating an example of the operation of the radiation detection unit that is illustrated in FIG. 2.

FIG. 3 is a timing chart for illustrating an example of the operation of the radiation detection unit 1100 that is illustrated in FIG. 2. A method of detecting the start of radiation irradiation in the radiation detection unit 1100 is described with reference to FIG. 3. In FIG. 3, the horizontal axis is the time axis.

Dark electric charges are constantly generated in the sensor array 1120, and dark electric charge resetting operation therefore needs to be executed regularly. To that end, as illustrated in FIG. 3, a change in the current amount of a bias line is detected while executing reset scanning (TC101) in which rows of the sensor array 1120 are driven one by one to turn the switching elements 1123 on and to reset the electric charges of each pixel 1121 that is connected to the target row. When the irradiation of a radiation ray is started, electric charges are generated in each pixel 1121 and, at that instant, electric charges flow into the bias line out of each pixel 1121 in the row where the switching elements 1123 are turned on for reset scanning, resulting in a rapid increase in the current amount of the bias line. The rapid increase is used to detect the start of radiation irradiation, the reset scanning of the row where the reset scanning has been executed is stopped (TC102) at the instant of the detection, and the switching elements 1123 are turned off to enter the operation of accumulating image signal charges that are generated from a radiation ray (TC103).

After the radiation irradiation is ended, the rows of the sensor array 1120 are again driven one by one to turn the switching elements 1123 on and to execute the operation of reading the electric charges of radiographic image signals that have been accumulated in each pixel 1121 (TC104). In this operation, some of effective electric charges generated by radiation irradiation flow out of the pixels 1121 in the row where the reset operation has been executed at the time the start of radiation irradiation has been detected, because the switching element 1123 in each of those pixels 1121 has been turned on. Pixel data of the pixels 1121 in the row where effective electric charges have flowed out is smaller in electric charge amount than pixel data in the preceding or following row, and is not reliable. The unreliable pixel data receives correction processing such as interpolation that uses normal pixel data of the surrounding rows. With this configuration, the radiation imaging apparatus 1000-1 can automatically detect radiation irradiation on its own and store a captured image in its internal storing unit 1340, thereby eliminating the need to build a configuration for communication between the radiation generation apparatus 2000 and the radiation imaging apparatus 1000-1.

Referring back to FIG. 1, the irradiation detection unit 1200 detects the start and end of radiation irradiation.

The control unit 1300-1 is a component that controls the operation in the radiation imaging apparatus 1000-1 in an integrated manner, and controls, for example, radiographic image capturing and communication operation. The control unit 1300-1 reads, for example, a program stored in the storing unit 1340 to control the operation in the radiation imaging apparatus 1000-1 in an integrated manner based on the program. Besides, the control unit 1300-1 may control the radiation imaging apparatus 1000-1 with the use of a control signal generating circuit such as an ASIC, or may control the radiation imaging apparatus 1000-1 by using the program and the control signal generating circuit described above in combination. The control unit 1300-1 includes, as illustrated in FIG. 1, the image capturing control unit 1310, an internal clock 1320, an image capturing information management unit 1330, the storing unit 1340, and a communication control unit 1350.

The image capturing control unit 1310 controls the driving of the radiation detection unit 1100 and radiographic image capturing which involves the obtaining of an image. To give a specific example, the image capturing control unit 1310 controls radiographic image capturing in order to obtain a captured image that reflects the intensity distribution of radiation detected by the radiation detection unit 1100.

The internal clock 1320 serves as an imaging apparatus time management unit configured to manage the time on the radiation imaging apparatus 1000-1 as an imaging apparatus time.

The image capturing information management unit 1330 manages, in association with the captured image 1341, image capturing information 1342, which includes at least the ID of the radiation imaging apparatus 1000-1, patient information (subject information), and image capturing time information.

The storing unit 1340 stores the image capturing information 1342, which includes at least image capturing time information about the date/time of execution of radiographic image capturing which is determined based on the imaging apparatus time managed by the internal clock 1320, in association with the captured image 1341, which is obtained by this session of radiographic image capturing.

The image capturing information management unit 1330 includes a time correction unit 1331. The time correction unit 1331 obtains the system time, which is a reference time of the radiation imaging system 1 managed by a system time management unit 4100, and corrects the image capturing time information of the image capturing information 1342 based on the amount of a time disparity between the imaging apparatus time managed by the internal clock 1320 and the obtained system time. The time correction unit 1331 further makes a correction so that the imaging apparatus time managed by the internal clock 1320 is matched to the system time managed by the system time management unit 4100. The time correction unit 1331 executes the correction of the imaging apparatus time by obtaining the system time from the system time management unit 4100 when the connection unit 1700 for connection to the cradle 3000-1, which is a type of external apparatus, is connected to the cradle 3000-1. When the imaging apparatus time is corrected by the time correction unit 1331, the radiation imaging apparatus 1000-1 stores a history that includes the pre-correction imaging apparatus time and the post-correction imaging apparatus time in, for example, the storing unit 1340. The radiation imaging apparatus 1000-1 also attaches time correction-completed information to a piece of the image capturing information 1342 that has been corrected in image capturing time information by the time correction unit 1331, in order to avoid correcting the corrected image capturing time information again next time the time correction unit 1331 corrects the imaging apparatus time.

The communication control unit 1350 controls communication to and from the cradle 3000-1, for example. To give a specific example, the communication control unit 1350 controls the transmission of a piece of the image capturing information 1342 that has been corrected in image capturing time information by the time correction unit 1331 and the captured image 1341 that is stored in association with the piece of the image capturing information 1342 to the cradle 3000-1. The communication control unit 1350, which executes this transmission control, serves as a transmission control unit.

The image processing unit 1400 performs various types of image processing as necessary on image data of a radiographic image that is a captured image generated by the radiation detection unit 1100. The image data of the radiographic image on which image processing has been performed by the image processing unit 1400 is sent to the control unit 1300-1 and stored in the storing unit 1340. The image processing unit 1400 includes the A/D converter 1410 configured to convert a captured image that is formed from analog signals generated by the radiation detection unit 1100 into a captured image that is formed from digital signals.

The state notification unit 1500 is used to notify the state of the radiation imaging apparatus 1000-1.

The battery 1600 is a rechargeable power supply unit used to run the radiation imaging apparatus 1000-1.

The connection unit 1700 is used to connect to the cradle 3000-1, which is a type of external apparatus.

The cradle 3000-1 includes a connection unit 3100, a control unit 3200-1, and a state display unit 3300.

The connection unit 3100 is used to connect to the radiation imaging apparatus 1000-1.

The control unit 3200-1 is used to control the operation in the cradle 3000-1 in an integrated manner, and controls the exchange of data and information between the cradle 3000-1 and the radiation imaging apparatus 1000-1 and between the cradle 3000-1 and the console 4000. The control unit 3200-1 includes a communication control unit 3210 and a charging control unit 3220.

The communication control unit 3210 controls, for example, communication between the cradle 3000-1 and the radiation imaging apparatus 1000-1 and between the cradle 3000-1 and the console 4000. To give a specific example, the communication control unit 3210 controls the reception of the image capturing information 1342 (which includes at least image capturing conditions, patient information (subject information), and image capturing time information) and the captured image 1341 that are transmitted from the radiation imaging apparatus 1000-1 by the communication control unit 1350. The communication control unit 3210, which executes this reception control, serves as a reception control unit.

The charging control unit 3220 performs control in which the battery 1600 is charged when the cradle 3000-1 is connected to the radiation imaging apparatus 1000-1 via the connection unit 3100.

The state display unit 3300 is used to display the state of the radiation imaging apparatus 1000-1.

The cradle 3000-1 may be configured such that, instead of a single radiation imaging apparatus 1000-1, a plurality of radiation imaging apparatus 1000-1 can be connected simultaneously to the cradle 3000-1 for charging and for communication.

The console 4000 includes, for example, a personal computer that includes a display unit 4200. The console 4000 includes the system time management unit 4100 configured to manage the system time, which is corrected via the intra-hospital network 5000 and which is a reference time of the radiation imaging system 1.

The console 4000 can receive an image capturing order for radiographic image capturing from the HIS/RIS 6000, which is connected to the console 4000 through the intra-hospital network 5000, and set image capturing information that includes image capturing conditions and patient information (subject information) specified in the image capturing order in the radiation imaging apparatus 1000-1 through the cradle 3000-1. The console 4000 can also receive the captured image 1341 transferred from the radiation imaging apparatus 1000-1 through the cradle 3000-1, perform image processing for diagnosis, and transfer the processed image to the HIS/RIS 6000 over the intra-hospital network 5000. With the console 4000, image capturing information such as patient information (subject information) can be entered later for the captured image 1341 that has been captured without the advance setting of image capturing information that reflects an image capturing order. The display unit 4200 displays the captured image 1341, the image capturing information 1342, and a user interface on which the image capturing information 1342 is edited.

An example of the flow of radiographic image capturing processing by the radiation imaging system 1 according to this embodiment is described next.

First, the radiation imaging apparatus 1000-1 is connected to the cradle 3000-1 in order to charge the battery 1600 of the radiation imaging apparatus 1000-1. When detecting the connection to the radiation imaging apparatus 1000-1, the cradle 3000-1 uses the charging control unit 3220 to start controlling the charging of the battery 1600, and changes the status displayed on the state display 3300 of the cradle 3000-1 to "charging". In the case where the battery 1600 of the radiation imaging apparatus 1000-1 has already been charged to full, the charging control unit 3220 stops the charging and the status displayed on the state display unit 3300 is changed to "charge completed". The time correction unit 1331 synchronizes the system time managed by the system time management unit 4100 of the console 4000 and the imaging apparatus time managed by the internal clock 1320 of the radiation imaging apparatus 1000-1 to correct a disparity of the imaging apparatus time. The radiation imaging apparatus 1000-1 stores the corrected imaging apparatus time T1 in the storing unit 1340, for example. The premise of the description given is that, at this point, the radiation imaging apparatus 1000-1 has not obtained a radiographic image yet.

The console 4000 receives an image capturing order for radiographic image capturing from the HIS/RIS 6000, and controls the radiation imaging apparatus 1000-1 through the cradle 3000-1 so that advance image capturing information, which includes image capturing conditions and patient information, is stored in advance as the image capturing information 1342 in the storing unit 1340. The image capturing information stored here is not limited to one, but a plurality of pieces of image capturing information can be stored in the storing unit 1340 of the radiation imaging apparatus 1000-1. Radiographic image capturing to obtain a captured image can be executed also when an image capturing order from the HIS/RIS 6000 is not submitted in advance and the image capturing information 1342 is not stored in the storing unit 1340 of the radiation imaging apparatus 1000-1 as a result.

Next, the radiation imaging apparatus 1000-1 is removed from the cradle 3000-1 in order to execute radiographic image capturing. When detecting the removal from the cradle 3000-1, the radiation imaging apparatus 1000-1 starts preparations for radiographic image capturing, and shifts to a state where the start of radiation irradiation can be detected. While the radiation imaging apparatus 1000-1 in this embodiment starts preparations for radiographic image capturing when detecting removal from the cradle 3000-1, preparations for radiographic image capturing may be started when, for example, a switch or a similar input unit that is provided on the radiation imaging apparatus 1000-1 is operated. In the case where the remaining power of the battery 1600 is not enough for image capturing, or in the case where the storing unit 1340 does not have a free capacity large enough to store the captured image 1341, the state notification unit 1500 displays that the radiation imaging apparatus 1000-1 is in a state where "image capturing is inexecutable". The state notification unit 1500, which is assumed here to be a visible light notification unit that uses a single or a plurality of LEDs or the like, may instead be, for example, a sound notification unit that uses a buzzer or the like.

When the irradiation of a radiation ray from the radiation generation apparatus 2000 is detected, the radiation imaging apparatus 1000-1 stores a radiographic image generated by the radiation detection unit 1100 in the storing unit 1340 as the captured image 1341. In the case where advance image capturing information has been set beforehand, the advance image capturing information is treated as the image capturing information 1342, and the captured image 1341 is stored in association with this image capturing information 1342. At the same time as the storing of the captured image 1341, image capturing execution information such as the ID information of the radiation imaging apparatus 1000-1 and imaging apparatus time information about the date/time of execution of the image capturing is obtained and stored as an addition to the image capturing information 1342. In the case where radiographic image capturing has been executed without advance image capturing information, only the image capturing execution information described above is stored in the storing unit 1340 as the image capturing information 1342. The same applies to the case where radiographic image capturing is executed a number of times, and the image capturing execution information of each session of radiographic image capturing is treated as the image capturing information 1342, and the captured image 1341 is stored in association with this image capturing information 1342.

The captured image 1341 and the image capturing information 1342 that are thus stored in the storing unit 1340 of the radiation imaging apparatus 1000-1 are transferred to the console 4000 through the cradle 3000-1 when the radiation imaging apparatus 1000-1 is connected to the cradle 3000-1. At this point, the time correction unit 1331, for example, synchronizes the system time managed by the system time management unit 4100 of the console 4000 and the imaging apparatus time managed by the internal clock 1320 of the radiation imaging apparatus 1000-1 in order to correct a time error between the system time and the imaging apparatus time. In the synchronization, the time correction unit 1331, for example, corrects the image capturing time information out of the image capturing information 1342 stored in the storing unit 1340 of the radiation imaging apparatus 1000-1 with reference to the system time based on the amount of correction (the amount of the disparity) between the system time and the imaging apparatus time. Details of this processing are described with reference to FIG. 4.

Figure 4:
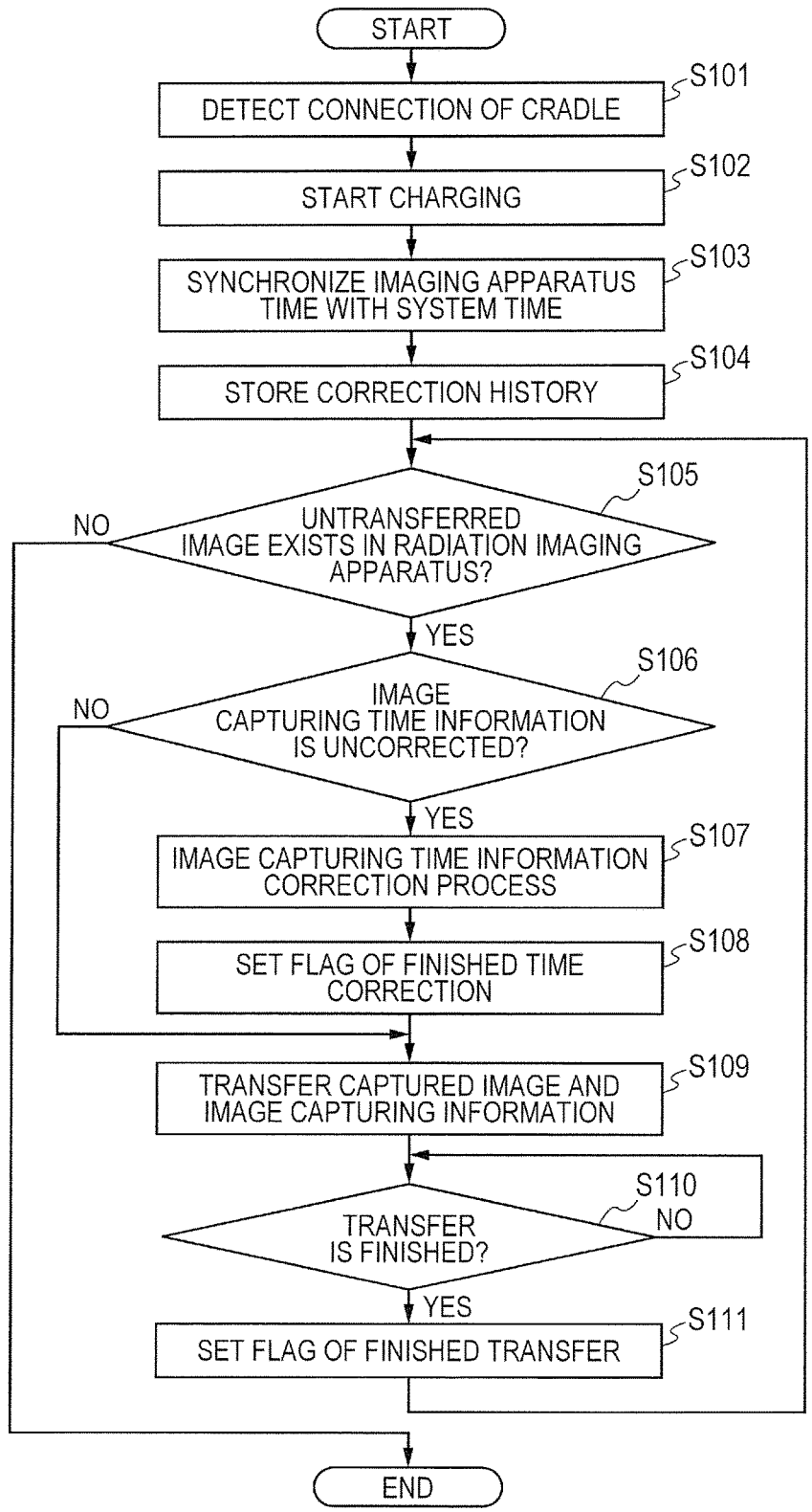
FIG. 4 is a flow chart for illustrating an example of processing steps in a method of controlling the radiation imaging system according to the first embodiment of the present invention.

FIG. 4 is a flow chart for illustrating an example of processing steps in a method of controlling the radiation imaging system 1 according to the first embodiment of the present invention. Specifically, the processing illustrated in FIG. 4 is one that is centered around processing of correcting the image capturing time information of the image capturing information 1342 described above.

When the radiation imaging apparatus 1000-1 is connected to the cradle 3000-1, the control unit 1300-1 of the radiation imaging apparatus 1000-1 and the control unit 3200-1 of the cradle 3000-1 detect the connection in Step S101.

In Step S102, the charging control unit 3220 of the cradle 3000-1 performs control to start charging the battery 1600 of the radiation imaging apparatus 1000-1.

The communication control unit 3210 of the cradle 3000-1 then obtains the system time managed by the system time management unit 4100 of the console 4000, and transmits the obtained system time to the radiation imaging apparatus 1000-1. In Step S103, the time correction unit 1331 of the radiation imaging apparatus 1000-1 obtains the system time transmitted from the console 4000, and corrects the imaging apparatus time managed by the internal clock 1320 by synchronization in which the imaging apparatus time is matched to the system time.

In Step S104, the radiation imaging apparatus 1000-1 (for example, the control unit 1300-1) stores in, for example, the storing unit 1340 a history that includes the imaging apparatus time prior to and after the correction of the imaging apparatus time of Step S103. Here, the post-correction imaging apparatus time, which is equal to the system time, is denoted by T2, the pre-correction imaging apparatus time is denoted by T2', for example, and this correction history is stored in, for example, the storing unit 1340 to be used in the correction of the image capturing time information described later.

In Step S105, the control unit 1300-1 of the radiation imaging apparatus 1000-1 determines whether or not an image that has not been transferred yet is left in the storing unit 1340 of the radiation imaging apparatus 1000-1. When determining that there is no untransferred image (Step S105: No), the control unit 1300-1 determines that new radiographic image capturing is not being executed, and the processing of the flow chart of FIG. 4 is ended without executing image transfer processing.

When it is determined, in Step S105 that there is an untransferred linage (Step S105: Yes), on the other hand, the processing proceeds to Step S106.

In Step S106, the image capturing information management unit 1330 of the radiation imaging apparatus 1000-1, for example, checks whether or not a flag of finished time correction, which is information about the completion of time correction, is attached to a piece of the image capturing information 1342 that is associated with this untransferred image, to thereby determine whether or not the image capturing time information that is included in this piece of the image capturing information 1342 is uncorrected.

When it is determined in Step S106 that the image capturing time information included in the piece of the image capturing information 1342 that is associated with the untransferred image in question is uncorrected (Step S106: Yes), the processing proceeds to Step S107.

In Step S107, the time correction unit 1331 of the radiation imaging apparatus 1000-1 executes processing of correcting the image capturing time information included in the piece of the image capturing information 1342 that is associated with the untransferred image in question, based on the amount of a time disparity between the imaging apparatus time and the system time.

In this embodiment, the correction processing executed in Step S107 is as follows.

When the time disparity between the imaging apparatus time and the system time is due to the insufficient precision of the internal clock 1320 in the radiation imaging apparatus 1000-1, the disparity in time is in proportion to the length of time elapsed since the last time the synchronization processing described above is executed. In the case where the pre-correction image capturing execution time that is recorded in the image capturing information 1342 is T11', the corrected image capturing execution time, T11, can be calculated with the use of the corrected imaging apparatus time of the last correction T1 and a correction ratio α by, for example, Expression (1).

$$T11=(T11'-T1)\alpha+T1 \qquad (1)$$

When the corrected imaging apparatus time of the last correction is T1, the pre-correction imaging apparatus time of this correction is T2', and the corrected imaging apparatus time of this correction is T2, the correction ratio α can be obtained by Expression (2).

$$\alpha=(T2-T1)/(T2-'-T1) \qquad (2)$$

In Step S108, the image capturing information management unit 1330 of the radiation imaging apparatus 1000-1, for example, records a history of the corrected image capturing time information in the piece of the image capturing information 1342 that is associated with the untransferred image in question, and records the image capturing time information with the flag of finished time correction set thereto.

When the processing of Step S108 is finished, or when it is determined in Step S106 that the image capturing capturing information 1342 that is associated with the untransferred image in question is not uncorrected (i.e., has been corrected) (Step S106: No), the processing proceeds to Step S109.

In Step S109, the communication control unit 1350 of the radiation imaging apparatus 1000-1 performs control to transfer (transmit) the captured image 1341 that is the untransferred image in question and the piece of the image capturing information 1342 that is associated with this captured image 1341 to the cradle 3000-1. The captured image 1341 and image capturing information 1342 transferred (transmitted) to the cradle 3000-1 are left in the storing unit 1340 in this embodiment.

In Step S110, the control unit 1300-1 (for example, the communication control unit 1350) of the radiation imaging apparatus 1000-1 determines whether or not the transfer of Step S109 has been completed. When it is determined as a result that the transfer of Step S109 has not been completed (Step S110: No), the processing stands still at Step S109 until the transfer of Step S109 is completed.

When it is determined in Step S110 that the transfer of Step S109 has been completed (Step S110: Yes), on the other hand, the processing proceeds to Step S111.

In Step S111, the control unit 1300-1 of the radiation imaging apparatus 1000-1 sets a flag of finished transfer to the captured image 1341 and the image capturing information 1342 that have been left in the storing unit 1340 and transferred (transmitted) in Step S109, and records the captured image 1341 and the image capturing information 1342.

The captured image 1341 and the image capturing information 1342 to which the flag of finished transfer is attached in this manner cam be overwritten when new radiographic image capturing is executed. The captured image 1341 to which the flag of finished transfer is attached can be selected to be transferred again by operating the console 4000 if this captured image 1341 has been left in the storing unit 1340 of the radiation imaging apparatus 1000-1.

After the flag of finished transfer is set in Step S111, the processing returns to Step S105 to determine again whether or not there is an untransferred image in the radiation imaging apparatus 1000-1.

The processing of correcting the image capturing time information is executed for every untransferred image in this manner, and the whole processing is continued until the transfer to the cradle 3000-1 is completed for every untransferred image. The processing illustrated in the flow chart of FIG. 4 is merely an example, and the order of the processing steps may be rearranged or a processing step may be newly added or deleted as long as the modification does not depart significantly from what makes the present invention.

Thus, even when the imaging apparatus time does not match the system time due to an error, the image capturing time information of the image capturing information 1342 associated with the captured image 1341 can be corrected with reference to the system time by correcting the image capturing time information through synchronization with the system time.

A case is considered in which, after an imaging apparatus time T2' is synchronized with a system time T2 by connecting the radiation imaging apparatus 1000-1 to the cradle 3000-1, radiation image capturing is executed at an imaging apparatus time T21', thereby using up the battery 1600, which runs the internal clock 1320, before the radiation imaging apparatus 1000-1 is reconnected to the cradle 3000-1. In this case, the internal clock 1320 of the radiation imaging apparatus 1000-1 stops and the pre-correction imaging apparatus time is therefore unreliable when the imaging apparatus time is synchronized as the radiation imaging apparatus 1000-1 is reconnected to the cradle 3000-1. The time correction unit 1331 in this case executes time correction that only involves setting the internal clock 1320 to a system time T3, and the image capturing time information is corrected with the use of the history of time correction of the past.

The correction ratio α described above can be calculated by using a history that includes the corrected imaging apparatus time T1 of the past correction, the pre-correction imaging apparatus time T2' of the subsequent correction, and the corrected imaging apparatus time T2 of the subsequent correction. This is applied to calculate a corrected imaging apparatus time T21, which is obtained by correcting the pre-correction imaging apparatus time T21', which indicates the date/time of image capturing executed after the corrected imaging apparatus time T2, by, for example, Expression (3).

$$T21 = (T21' - T2)\alpha + T2 \qquad (3)$$

The correction ratio α can thus be calculated when a history of successive corrections is available. The correction ratio α may be calculated from the latest correction history, or, for example, an average of correction ratios calculated from a plurality of correction histories may be used as α. However, in the case where a history of past correction is not available, the correction of the image capturing time information is not executed and uncorrected image capturing time information is transferred to the cradle 3000-1.

The console 4000 receives the captured image 1341 and, in the case where advance image capturing information that includes patient information (subject information) has not been set to this captured image, image capturing information can be entered on the console 4000 to be set to the captured image. A captured image is checked and subjected to necessary image processing on the console 4000, and then the captured image and its associated image capturing information are transferred to the RIS over the intra-hospital network 5000.

According to this embodiment, the radiation imaging apparatus 1000-1 has an automatic radiation detection function, and radiographic image capturing can thus be executed freely by the radiation imaging apparatus alone without needing control via the console 4000 and communication to and from the radiation generation apparatus 2000. In addition, a simple system that does not need to connect a cable for image transfer and to build a wireless communication environment can be built by transferring the captured images 1341 that have been stocked in the radiation imaging apparatus 1000-1 when the radiation imaging apparatus 1000-1 is connected to the cradle 3000-1. This embodiment also allows for the correction of image capturing time information, which indicates the date/time of execution of image capturing, with reference to the system time before the image is transferred. This prevents pieces of time information of captured images from deviating from the actual order of execution of image capturing even when, for example, the captured images have been captured by a plurality of imaging apparatus among which there is a disparity in imaging apparatus time and transferred to the console 4000. Accordingly, the risk of wrong association between a captured image and a piece of image capturing information is reduced even when, for example, image capturing information that includes patient information (subject information) is entered later on the console 4000. In other words, in the case where a captured image is associated later with image capturing information that includes subject information, the risk of wrong association between a captured image and a piece of image capturing information is reduced with a simple configuration.

While this embodiment describes an example in which the captured image 1341 is transferred to the console 4000 via the cradle 3000-1, the present invention is not limited thereto. For instance, the console 4000 and the radiation imaging apparatus 1000-1 may be connected directly by a cable for the Ethernet (trademark) to transfer an image. In this case, after the radiation imaging apparatus 1000-1 is connected to the console 4000, the time kept by the radiation imaging apparatus 1000-1 and the time kept by the console 4000 are synchronized directly with the use of cable communication, the radiation imaging apparatus 1000-1 corrects the image capturing time information, and then image transfer is executed. Communication between the console 4000 and the radiation imaging apparatus 1000-1 may be wireless communication, instead of cable communication.

To immediately determine whether or not an image has been captured properly, a simple image for preview may be generated by, for example, thinning out and reducing in size the captured image 1341, and the preview image may be transferred to a preview image display apparatus (not shown) before the captured image 1341 is transferred to the console 4000. A portable terminal such as a wireless display or a smart device can be used as the preview image display apparatus. In this case, however, a wireless communication control unit, for example, needs to be provided in the radiation imaging apparatus 1000-1 for the transfer of a preview image.

While the console 4000 in the described example is a personal computer, the radiation imaging system 1 can be controlled also by a portable information terminal such as a tablet PC or a smart device. The present invention is also not limited to the described case where the time correction of the image capturing time information is executed in the radiation imaging apparatus 1000-1. The processing of correcting the time of the image capturing time information may be executed by, for example, the cradle 3000-1 or by software on the console 4000.

The radiation imaging system 1 of this embodiment described above executes the following processing.

The radiation imaging apparatus 1000-1 includes the internal clock 1320 to manage an imaging apparatus time within the radiation imaging apparatus. The radiation imaging apparatus 1000-1 uses the imaging apparatus time to store the image capturing information 1342, which includes at least image capturing time information, in the storing unit 1340 in association with the captured image 1341 when radiographic image capturing is executed. In the case where an image capturing order is received in advance, the radiation imaging apparatus 1000-1 stores advance image capturing information, which includes, for example, patient information (subject information), in the storing unit 1340 beforehand, and the captured image 1341 is associated with a relevant piece of the image capturing information 1342 when image capturing is executed. In this step, image capturing information that is generated at the time of execution of image capturing and that includes image capturing time information is stored as an addition to the advance image capturing information. In the case where an image capturing order Is not received in advance, only image capturing information that is generated at the time of execution of image capturing and that includes image capturing time information is stored as the image capturing information 1342. Without advance image capturing information, the radiation imaging apparatus 1000-1 transfers the captured image 1341 and the image capturing information 1342 to an external apparatus such as the console 4000 by, for example, connecting to the cradle 3000-1. The lacking image capturing information such as patient information can be set later on an input screen of the console 4000.

In the radiation imaging system 1 according to this embodiment, when the radiation imaging apparatus 1000-1 is connected to the cradle 3000-1 in order to, for example, charge the battery 1600 of the radiation imaging apparatus 1000-1 or transfer an image, the imaging apparatus time is synchronized with a system time, which is managed by the console 4000 and which serves as the reference. The synchronization includes correction in which the image capturing time information of the image capturing information 1342 associated with the captured image 1341 is corrected with reference to the system time based on the amount of correction (the amount of time disparity) of the imaging apparatus time. Thereafter, the captured image 1341 and the image capturing information 1342 that now includes the corrected image capturing time information are transferred to the console 4000 via the cradle 3000-1.

The risk of wrong association between a captured image and a piece of image capturing information can thus be reduced with a simple configuration in the case where image capturing information that includes subject information is associated with a captured image at a later point.

Second Embodiment

Next, a second embodiment of the present invention is described.

Figure 5:
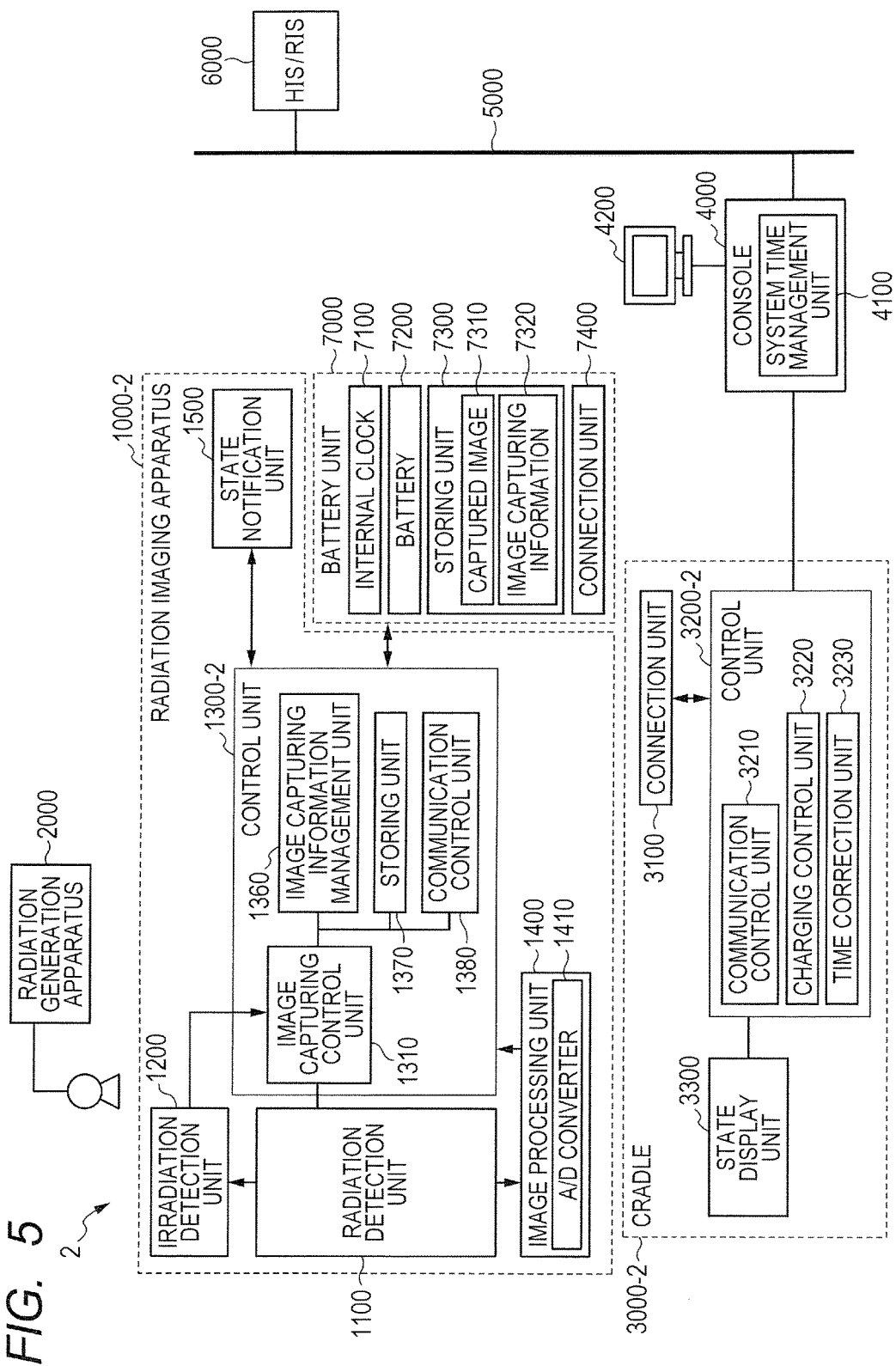
FIG. 5 is a diagram for illustrating an example of the schematic configuration of a radiation imaging system according to a second embodiment of the present invention.

FIG. 5 is a diagram for illustrating an example of the schematic configuration of a radiation imaging system 2 according to the second embodiment of the present invention. In FIG. 5, components that are the same as those in FIG. 1, which is a diagram for illustrating the schematic configuration of the radiation imaging system 1 according to the first embodiment, are denoted by the same reference symbols, and detailed descriptions thereof are omitted here.

The radiation imaging system 2 according to this embodiment includes, as illustrated in FIG. 5, a radiation imaging apparatus 1000-2, a radiation generation apparatus 2000, a cradle 3000-2, a console 4000, an intra-hospital network 5000, an HIS/RIS 6000, and a battery unit 7000. Specifically, the radiation imaging system 2 of this embodiment is a system that includes the radiation imaging apparatus 1000-2 configured to obtain a captured image by radiographic image capturing of a subject, the battery unit 7000, which is a portable power supply apparatus that includes a rechargeable battery 7200 for running the radiation imaging apparatus 1000-2 and that is removably mounted to the radiation imaging apparatus 1000-2, and external apparatus (the cradle 3000-2, the console 4000, and the HIS/RIS 6000), which can be electrically connected to the battery unit 7000.

The radiation imaging apparatus 1000-2 includes, as illustrated in FIG. 5, a radiation detection unit 1100, an irradiation detection unit 1200, a control unit 1300-2, an image processing unit 1400, and a state notification unit 1500.

As in the first embodiment, the radiation detection unit 1100 detects radiation and generates image data of a radiographic image that is a captured image. The detailed configuration of this radiation detection unit 1100 is the same as the one in the first embodiment. The irradiation detection unit 1200 detects the start and end of radiation irradiation as in the first embodiment. The image processing unit 1400 performs various types or image processing as necessary on image data of a radiographic image that is a captured image generated by the radiation detection unit 1100, as in the first embodiment. The state notification unit 1500 is used to notify the state of the radiation imaging apparatus 1000-2. The battery unit 7000 removably mounted to the radiation imaging apparatus 1000-2 feeds power to the radiation imaging apparatus 1000-2.

The control unit 1300-2 is a component that controls the operation in the radiation imaging apparatus 1000-2 in an integrated manner, and controls, for example, radiographic image capturing and communication operation. The control unit 1300-2 reads, for example, a program stored in a storing unit 1370 to control the operation in the radiation imaging apparatus 1000-2 in an integrated manner based on the program. Besides, the control unit 1300-2 may control the radiation imaging apparatus 1000-2 with the use of a control signal generating circuit such as an ASIC, or may control the radiation imaging apparatus 1000-2 by using the program and the control signal generating circuit described above in combination. The control unit 1300-2 includes, as illustrated in FIG. 5, the image capturing control unit 1310, an image capturing information management unit 1360, the storing unit 1370, and a communication control unit 1380.

The image capturing control unit 1310 controls the driving of the radiation detection unit 1100 and radiographic image capturing which involves the obtaining of an image as in the first embodiment.

The image capturing information management unit 1360 manages, in association with a captured image 7310, image capturing information 7320, which includes at least the ID of the radiation imaging apparatus 1000-2, patient information (subject information), and image capturing time information.

The storing unit 1370 temporarily stores digital captured image data obtained by radiographic image capturing, and stores various types of information and programs.

The communication control unit 1380 controls communication between the radiation imaging apparatus 1000-2 and the battery unit 7000 and between the radiation imaging apparatus 1000-2 and the external apparatus described above. For example, the communication control unit 1380 controls the transmission of a piece of the image capturing information 7320 stored in a storing unit 7300 of the battery unit 7000 and the captured image 7310 that is associated with the piece of the image capturing information 7320 and stored in the storing unit 7300 to the cradle 3000-2. The communication control unit 1380, which executes this transmission control, constructs a transmission control unit.

The battery unit 7000 includes, as illustrated in FIG. 5, an internal clock 7100, a battery 7200, the storing unit 7300, and a connection unit 7400.

The internal clock 7100 serves as an imaging apparatus time management unit configured to manage the time on the radiation imaging apparatus 1000-2 as an imaging apparatus time.

The battery 7200 is a rechargeable power supply unit used to run the radiation imaging apparatus 1000-2.

The storing unit 7300 stores the image capturing information 7320, which includes at least image capturing time information about the date/time of execution of radiographic image capturing which is determined based on the imaging apparatus time managed by the internal clock 7100, in association with the captured image 7310, which is obtained by this session of radiographic image capturing.

The connection unit 7400 is used to connect to the cradle 3000-2, which is a type of external apparatus.

The cradle 3000-2 includes, as illustrated in FIG. 5, the connection unit 3100, a control unit 3200-2, and the state display unit 3300. The cradle 3000-2 may be configured such that, instead of a single battery unit 7000, a plurality of battery units 7000 can be connected simultaneously for charging and for communication.

The connection unit 3100 is used to connect to the battery unit 7000.

The control unit 3200-2 is a component that controls the operation in the cradle 3000-2 in an integrated manner, and controls the exchange of data and information between the cradle 3000-2 and the radiation imaging apparatus 1000-2, between the cradle 3000-2 and the battery unit 7000, and between the cradle 3000-2 and the console 4000. The control unit 3200-2 includes the communication control unit 3210, the charging control unit 3220, and a time correction unit 3230.

The communication control unit 3210 controls, for example, the communication (transmission and reception) of various images and various types of information between the cradle 3000-2 and the radiation imaging apparatus 1000-2, between the cradle 3000-2 and the battery unit 7000, and between the cradle 3000-2 and the console 4000. To give a specific example, the communication control unit 3210 controls the reception of the image capturing information 7320 and the captured linage 7310 that are transmitted from the communication control unit 1380. The communication control unit 3210, which executes this reception control, serves as a reception control unit.

The charging control unit 3220 performs control in which the battery 7200 is charged when the cradle 3000-2 is connected to the battery unit 7000 via the connection unit 3100.

The time correction unit 3230 obtains a system time, which is a reference time of the radiation imaging system 2 managed by the system time management unit 4100, and corrects the image capturing time information of the image capturing information 7320 based on the amount of a time disparity between the imaging apparatus time managed by the internal clock 7100 and the obtained system time. The time correction unit 3230 further makes a correction so that the imaging apparatus time managed by the internal clock 7100 is matched to the system time managed by the system time management unit 4100. The time correction unit 3230 executes the correction of the imaging apparatus time by obtaining the system time from the system time management unit 4100 when the cradle 3000-2 and the battery unit 7000 are connected. When the imaging apparatus time is corrected by the time correction unit 3230, the radiation imaging system 2 stores a history that includes the pre-correction imaging apparatus time and the post-correction imaging apparatus time in, for example, the storing unit 7300 of the battery unit 7000. The radiation imaging system 2 also attaches time correction-completed information to a piece of the image capturing information 7320 that has been corrected in image capturing time information by the time correction unit 3230, in order to avoid correcting the corrected image capturing time information again next time the time correction unit 3230 corrects the imaging apparatus time.

In this embodiment, a time correction unit is provided in the cradle 3000, whereas the time correction unit in the first embodiment described above is provided in the radiation imaging apparatus 1000.

The state display unit 3300 is used to display the state of the battery unit 7000 and the radiation imaging apparatus 1000-2.

An example of the flow of radiographic image capturing processing by the radiation imaging system 2 according to this embodiment is described next.

The battery unit 7000 is connected to the cradle 3000-2 in order to charge the battery 7200 of the battery unit 7000. When detecting the connection to the battery unit 7000, the cradle 3000-2 uses the charging control unit 3220 to start controlling the charging of the battery 7200. The method of the charging control and control performed on the state display unit 3300 of the cradle 3000 can be the same as those in the first embodiment. The cradle 3000-2 notifies information of the system time managed by the system time management unit 4100 of the console 4000 to the battery unit 7000 to synchronize the internal clock 7100 with the system time. A history that includes the imaging apparatus time prior to a time correction executed in the synchronization and the imaging apparatus time after the time correction is stored in, for example, the storing unit 7300 of the battery unit 7000.

The console 4000 receives an image capturing order for radiographic image capturing from the HIS/RIS 6000, and stores the image capturing order in advance as the image capturing information 7320 in the storing unit 7300 of the battery unit 7000 through the cradle 3000-2. The image capturing information stored here is not limited to one, but pieces of image capturing information from a plurality of image capturing orders can be stored. As in the first embodiment, radiographic image capturing to obtain a captured image can be executed also when an image capturing order is not submitted in advance and the image capturing information 7320 is not stored in the storing unit 7300 of the battery unit 7000 as a result.

Next, the battery unit 7000 is removed from the cradle 3000-2 and is connected to the radiation imaging apparatus 1000-2 in order to execute radiographic image capturing. When the battery unit 7000 is connected to and feeds power to the radiation imaging apparatus 1000-2, thereby activating the radiation imaging apparatus 1000-2, the radiation imaging apparatus 1000-2 starts preparations for radiographic image capturing, and shifts to a state where the start of radiation irradiation can be detected. While the radiation imaging apparatus 1000-2 in this embodiment starts preparations for radiographic image capturing when the battery unit 7000 is connected, preparations for radiographic image capturing may be started when, for example, a switch or a similar input unit that is provided on the radiation imaging apparatus 1000-2 is operated. The method of notifying the state of the battery unit 7000 such as the remaining power of the battery 7200 and the lack of a free capacity in the storing unit 7300 is the same as the one in the first embodiment.

The radiation imaging apparatus 1000-2 executes image capturing by radiography, temporarily stores a captured image obtained by the radiographic image capturing in the storing unit 1370 of the control unit 1300-2, and then transfers the captured image to the storing unit 7300 of the battery unit 7000. In the case where advance image capturing information has been set beforehand, the advance image capturing information is treated as the image capturing information 7320, and the captured image 7310 is stored in association with the image capturing information 7320. At the same time as the storing of the captured image 7310, image capturing execution information such as the ID information of the radiation imaging apparatus 1000-2 and imaging apparatus time information about the date/time of execution of the image capturing that is determined with reference to the internal clock 7100 is obtained and stored as an addition to the image capturing information 7320. In the case where radiographic image capturing has been executed without advance image capturing information, only the image capturing execution information described above is stored as the image capturing information 7320 in the storing unit 7300 in association with the captured image 7310. The same applies to the case where radiographic image capturing is executed a number of times, and the image capturing execution information of each session of radiographic image capturing is treated as the image capturing information 7320, and the captured image 7310 is stored in association with the image capturing information 7320.

The captured image 7310 thus stored in the storing unit 7300 of the battery unit 7000 is transferred to the console 4000 through the cradle 3000-2 when the battery unit 7000 is connected to the cradle 3000-2. At this point, the time correction unit 3230, for example, synchronizes the system time managed by the system time management unit 4100 of the console 4000 and the imaging apparatus time managed by the internal clock 7100 of the battery unit 7000 in order to correct a time error between the system time and the imaging apparatus time. In the synchronization, the time correction unit 3230, for example, corrects the image capturing time information out of the image capturing information stored in the storing unit 7300 of the battery unit 7000 with reference to the system time based on the amount of correction (the amount of the disparity) between the system time and the imaging apparatus time. Details of this time correction processing are the same as those in the first embodiment.

Thus, according to this embodiment, image capturing time information about the date/time of execution of image capturing can be corrected with reference to the system time before the image is transferred to the console 4000 as in the first embodiment. This prevents confusion arising from a disparity in time when, for example, image capturing information that includes patient information (subject information) is set manually on the console 4000 after image capturing is executed, and the risk of wrong association between a captured image and a piece of image capturing information is reduced as a result. In addition, the radiation imaging apparatus of this embodiment is improved in user-friendliness even more than that of the first embodiment because, in this embodiment, the radiation imaging apparatus can be charged by bringing only the battery unit 7000 to the cradle and, in the case where the remaining power of the battery 7200 becomes short in the middle of radiographic image capturing, the image capturing can be continued by replacing the spent battery unit 7000 with the charged battery unit 7000.

Other Embodiments

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-249261, filed Dec. 9, 2014, which is hereby incorporated by reference herein in its entirety.

What is claimed is:

1. A radiation imaging system, comprising;
a radiation imaging apparatus configured to obtain a captured image by radiographic image capturing of a subject; and
an external apparatus configured to be connectable to the radiation imaging apparatus,
the external apparatus comprising a system time management unit configured to manage a system time, which serves as a reference time of the radiation imaging system,
the radiation imaging apparatus comprising:
an imaging apparatus time management unit configured to manage an imaging apparatus time, which is a time on the radiation imaging apparatus;
a storing unit configured to store image capturing information in association with the captured image obtained by the radiographic image capturing, the image capturing information comprising at least image capturing time information about a date/time of execution of the radiographic image capturing which is determined based on the imaging apparatus time; and
a time correction unit configured to obtain the system time and to correct the image capturing time information based on an amount of a time disparity between the imaging apparatus time and the system time.

2. A radiation imaging system according to claim 1, wherein the time correction unit is further configured to make a correction so that the imaging apparatus time is matched to the system time.

3. A radiation imaging system according to claim 2, wherein, when the imaging apparatus time is corrected by the time correction unit, the radiation imaging apparatus is configured to store a history that comprises the imaging apparatus time prior to the correction and the imaging apparatus time after the correction.

4. A radiation imaging system according to claim 2, wherein the radiation imaging apparatus further comprises a connection unit configured to connect to the external apparatus, and
wherein, when the connection unit is connected to the external apparatus, the time correction unit is configured to obtain the system time to correct the imaging apparatus time.

5. A radiation imaging system according to claim 1, wherein the radiation imaging apparatus further comprises a transmission control unit configured to control transmission of the image capturing information that has been corrected in the image capturing time information by the time correction unit and the captured image that is stored in association with the image capturing information to the external apparatus, and
wherein the external apparatus further comprises a reception control unit configured to control reception of the image capturing information and the captured image that are transmitted from the radiation imaging apparatus by the transmission control unit.

6. A radiation imaging system according to claim 1, wherein the radiation imaging apparatus further comprises a rechargeable power supply unit configured to run the radiation imaging apparatus, and
wherein the external apparatus further comprises a charging control unit configured to control charging of the rechargeable power supply unit when the external apparatus is connected to the radiation imaging apparatus.

7. A radiation imaging system according to claim 2, wherein the radiation imaging apparatus is configured to attach time correction-completed information to the image capturing information that has been corrected in the image capturing time information by the time correction unit, in order to avoid correcting the corrected image capturing time information again next time the time correction unit corrects the imaging apparatus time.

8. A radiation imaging system, comprising:
a radiation imaging apparatus configured to obtain a captured image by radiographic image capturing of a subject;
a portable power supply apparatus comprising a rechargeable power supply unit configured to run the radiation imaging apparatus, the portable power supply apparatus being removably mounted to the radiation imaging apparatus; and
an external apparatus configured to be connectable to the portable power supply apparatus,
the portable power supply apparatus comprising:
an imaging apparatus time management unit configured to manage an imaging apparatus time, which is a time on the radiation imaging apparatus; and
a storing unit configured to store image capturing information in association with the captured image obtained by the radiographic image capturing, the image capturing information comprising at least image capturing time information about a date/time of execution of the radiographic image capturing which is determined based on the imaging apparatus time,
the external apparatus comprising:
a system time management unit configured to manage a system time, which serves as a reference time of the radiation imaging system; and
a time correction unit configured to obtain the imaging apparatus time and to correct the image capturing time information based on an amount of a time disparity between the imaging apparatus time and the system time.

9. A radiation imaging system according to claim 8, wherein the time correction unit is further configured to make a correction so that the imaging apparatus time is matched to the system time.

10. A radiation imaging system according to claim 9, wherein, when the imaging apparatus time is corrected by the time correction unit, the radiation imaging system is configured to store a history that comprises the imaging apparatus time prior to the correction and the imaging apparatus time after the correction.

11. A radiation imaging system according to claim 9, wherein, when the external apparatus and the portable power supply apparatus are connected to each other, the time correction unit is configured to correct the imaging apparatus time.

12. A radiation imaging system according to claim 8,
wherein the radiation imaging apparatus comprises a transmission control unit configured to control transmission of the image capturing information and the captured image that is stored in association with the image capturing information to the external apparatus, and
wherein the external apparatus further comprises a reception control unit configured to control reception of the linage capturing information and the captured image that are transmitted from the radiation imaging apparatus by the transmission control unit.

13. A radiation imaging system according to claim 8, wherein the external apparatus further comprises a charging control unit configured to control charging of the power supply unit when the external apparatus is connected to the portable power supply apparatus.

14. A radiation imaging system according to claim 9, wherein the radiation imaging system is configured to attach time correction-completed information to the image capturing information that has been corrected in the image capturing time information by the time correction unit, in order to avoid correcting the corrected image capturing time information again next time the time correction unit corrects the imaging apparatus time.

15. A radiation imaging system according to claim 1, wherein the radiation imaging apparatus further comprises:
a radiation detection unit comprising a plurality of radiation detection elements arranged two-dimensionally, the radiation detection unit being configured to detect a portion of a radiation ray that is transmitted through the subject; and
an image capturing control unit configured to control the radiographic image capturing in order to obtain the captured image that reflects an intensity distribution of radiation detected by the radiation detection unit.

16. A method of controlling a radiation imaging system that comprises a radiation imaging apparatus configured to obtain a captured image by radiographic image capturing of a subject, and an external apparatus configured to be connectable to the radiation imaging apparatus, the method comprising:
managing, by the external apparatus, a system time, which serves as a reference time of the radiation imaging system;
managing, by the radiation imaging apparatus, an imaging apparatus time, which is a time on the radiation imaging apparatus;
storing, by the radiation imaging apparatus, in a storing unit, image capturing information in association with the captured image obtained by the radiographic image capturing, the image capturing information comprising at least image capturing time information about a date/time of execution of the radiographic image capturing which is determined based on the imaging apparatus time; and
obtaining, by the radiation imaging apparatus, the system time and correcting the image capturing time information based on an amount of a time disparity between the imaging apparatus time and the system time.

17. A method of controlling a radiation imaging system that comprises a radiation imaging apparatus configured to obtain a captured image by radiographic image capturing of a subject, a portable power supply apparatus comprising a rechargeable power supply unit configured to run the radiation imaging apparatus, the portable power supply apparatus being removably mounted to the radiation imaging apparatus, and an external apparatus configured to be connectable to the portable power supply apparatus, the method comprising:
managing, by the portable power supply apparatus, an imaging apparatus time, which is a time on the radiation imaging apparatus;
storing, by the portable power supply apparatus, in a storing unit, image capturing information in association with the captured image obtained by the radiographic image capturing, the image capturing information comprising at least image capturing time information about a date/time of execution of the radiographic image capturing which is determined based on the imaging apparatus time;
managing, by the external apparatus, a system time, which serves as a reference time of the radiation imaging system; and
obtaining, by the external apparatus, the imaging apparatus time and correcting the image capturing time information based on an amount of a time disparity between the imaging apparatus time and the system time.

18. A non-transitory computer-readable storage medium having stored thereon a computer program for causing a computer to execute a method of controlling a radiation imaging system that comprises a radiation imaging apparatus configured to obtain a captured image by radiographic image capturing of a subject, and an external apparatus configured to be connectable to the radiation imaging apparatus, the method comprising:
managing, by the external apparatus, a system time, which serves as a reference time of the radiation imaging system;
managing, by the radiation imaging apparatus, an imaging apparatus time, which is a time on the radiation imaging apparatus;
storing, by the radiation imaging apparatus, in a storing unit, image capturing information in association with the captured image obtained by the radiographic image capturing, the image capturing information comprising at least image capturing time information about a date/time of execution of the radiographic image capturing which is determined based on the imaging apparatus time; and
obtaining, by the radiation imaging apparatus, the system time and correcting the image capturing time information based on an amount of a time disparity between the imaging apparatus time and the system time.

19. A non-transitory computer-readable storage medium having stored thereon a computer program for causing a computer to execute a method of controlling a radiation imaging system that comprises a radiation imaging apparatus configured to obtain a captured image by radiographic image capturing of a subject, a portable power supply apparatus comprising a rechargeable power supply unit configured to run the radiation imaging apparatus, the portable power supply apparatus being removably mounted to the radiation imaging apparatus, and an external apparatus configured to be connectable to the portable power supply apparatus, the method comprising:

managing, by the portable power supply apparatus, an imaging apparatus time, which is a time on the radiation imaging apparatus;

storing, by the portable power supply apparatus, in a storing unit, image capturing information in association with the captured image obtained by the radiographic image capturing, the image capturing information comprising at least image capturing time information about a date/time of execution of the radiographic image capturing which is determined based on the imaging apparatus time;

managing, by the external apparatus, a system time, which serves as a reference time of the radiation imaging system; and obtaining, by the external apparatus, the imaging apparatus time and correcting the image capturing time information based on an amount of a time disparity between the imaging apparatus time and the system time.

* * * * *